(12) United States Patent
Chen

(10) Patent No.: US 8,113,490 B2
(45) Date of Patent: Feb. 14, 2012

(54) WIND-WATER ULTRASONIC HUMIDIFIER

(76) Inventor: Hui-Chin Chen, Shanghai (CN)

( * ) Notice: Subject to any disclaimer, the term of this patent is extended or adjusted under 35 U.S.C. 154(b) by 355 days.

(21) Appl. No.: 12/567,794

(22) Filed: Sep. 27, 2009

(65) Prior Publication Data

US 2011/0074052 A1    Mar. 31, 2011

(51) Int. Cl.
 *B01F 3/04* (2006.01)
(52) U.S. Cl. ........... 261/81; 261/DIG. 14; 261/DIG. 48; D23/356
(58) Field of Classification Search ............. 261/1, 81, 261/DIG. 14, DIG. 48, DIG. 65; 239/102.2; D23/356, 360, 364, 366
See application file for complete search history.

(56) References Cited

U.S. PATENT DOCUMENTS

| | | | | |
|---|---|---|---|---|
| 1,718,182 A | * | 6/1929 | Rose et al. | 239/49 |
| D208,514 S | * | 9/1967 | Hartwell | D24/203 |
| 4,031,171 A | * | 6/1977 | Asao et al. | 261/1 |
| 4,113,809 A | * | 9/1978 | Abair et al. | 261/81 |
| 4,752,422 A | * | 6/1988 | Uchida et al. | 261/81 |
| 4,776,990 A | * | 10/1988 | Verity | 261/128 |
| 4,853,161 A | * | 8/1989 | Huang | 261/81 |
| 6,895,772 B2 | * | 5/2005 | Johnson et al. | 62/314 |
| 6,994,328 B2 | * | 2/2006 | Watkins et al. | 261/26 |
| D555,236 S | * | 11/2007 | Snow et al. | D23/356 |
| 2007/0035044 A1 | * | 2/2007 | Chiu | 261/81 |
| 2007/0069404 A1 | * | 3/2007 | Chi | 261/81 |
| 2007/0278702 A1 | * | 12/2007 | French et al. | 261/79.2 |

FOREIGN PATENT DOCUMENTS

JP         54-68041 A   *   5/1979   ................... 261/81

* cited by examiner

*Primary Examiner* — Richard L Chiesa
(74) *Attorney, Agent, or Firm* — Wang Law Firm, Inc.; Li K. Wang

(57) ABSTRACT

A wind-water ultrasonic humidifier includes a housing, a hollow connecting portion, a water circulation system, and a power control box. The water circulation system includes an electric base, a rubber cork plugged into the top of the water circulation system and having a baffle inserted into a concave hole, a circular threaded pipe including a nebulizer and a water pump, two arc-shaped bridging support stands provided for connecting both sides of the electric base in an arc shape, a latch structure disposed at a lower end of the support stand, latches disposed on both sides of the electric base, and a water dripping device installed at an upper end of the bridging support stand.

5 Claims, 3 Drawing Sheets

US 8,113,490 B2

WIND-WATER ULTRASONIC HUMIDIFIER

BACKGROUND OF THE INVENTION

1. Field of the Invention

The present invention relates to a wind-water ultrasonic humidifier.

2. Description of the Related Art

Present existing ultrasonic humidifiers generally require a fan to blow mists after water dripping and nebulization processes take place, and thus consume much electric power. Furthermore, the conventional ultrasonic humidifiers lack of artistic decorative appearance, expansion function, and fun.

SUMMARY OF THE INVENTION

Therefore, it is a primary objective of the present invention to overcome the aforementioned shortcoming and deficiency of the prior art by providing a wind-water ultrasonic humidifier designed with a wonderful concept and a bold innovation, and adopting a ceramic housing with simple, and fashioned decoration instead of the traditional dull and boring housing. As to the structure and functions of the wind-water ultrasonic humidifier, wonderful structure and circuit control are used for simulating a natural raindrop effect, and various different rain falling scenes can be adjusted according to users' personal need or preference to achieve a unique natural wind-water state of mind, and a water circulation system is used for achieving the effect of driving a fan by waterflow.

To achieve the foregoing objective, the present invention provides a wind-water ultrasonic humidifier comprising:

a housing;

a hollow connecting portion, whose top is coupled to the bottom of the housing for supplying electric power to the housing;

a water circulation system, installed in the housing, and including an electric base disposed at the top of the connecting portion, a rubber cork sheathed onto the top of the water circulation system and having a concave hole at the top of the rubber cork, a baffle inserted into the concave hole of the rubber cork and having a cylindrical support pillar at the bottom of the baffle, wherein the baffle is fixed precisely above the rubber cork, and a slender penetrating slot is formed at the middle of the baffle, and a nebulizer and a water pump are installed at both ends of the circular threaded pipe respectively, and both sides of the electric base are connected in a substantially arc shape by two arc bridging support stands, and a lower end of the support stand includes a protruded latching structure, and both sides of the electric base are designed with a latch containing space for receiving and latching the support stand, and an upper end of the bridging support stand includes a water dripping device; and a power control box, installed at the bottom of the hollow connecting portion.

The foregoing and other objectives and advantages of the present invention will become apparent with the detailed description of preferred embodiments and related drawings as follows.

Of course, another element and/or an arrangement of elements of the present invention may be altered or modified in an equivalent manner, and the invention is not limited to the preferred embodiments and drawings used in this specification only.

DETAILED DESCRIPTION OF THE PREFERRED EMBODIMENTS

Figure 1:
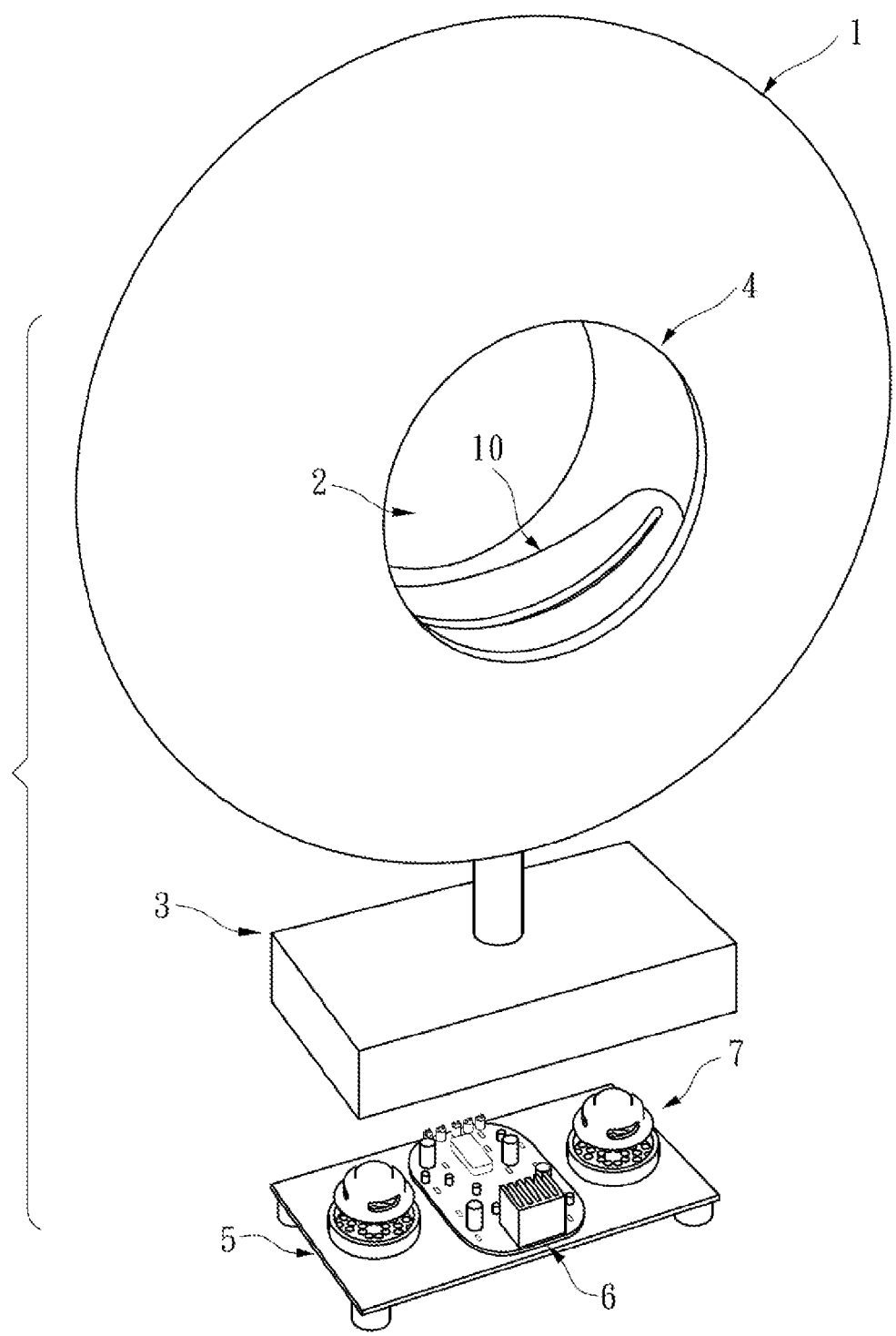
FIG. 1 is a perspective view of the present invention.
Figure 2:
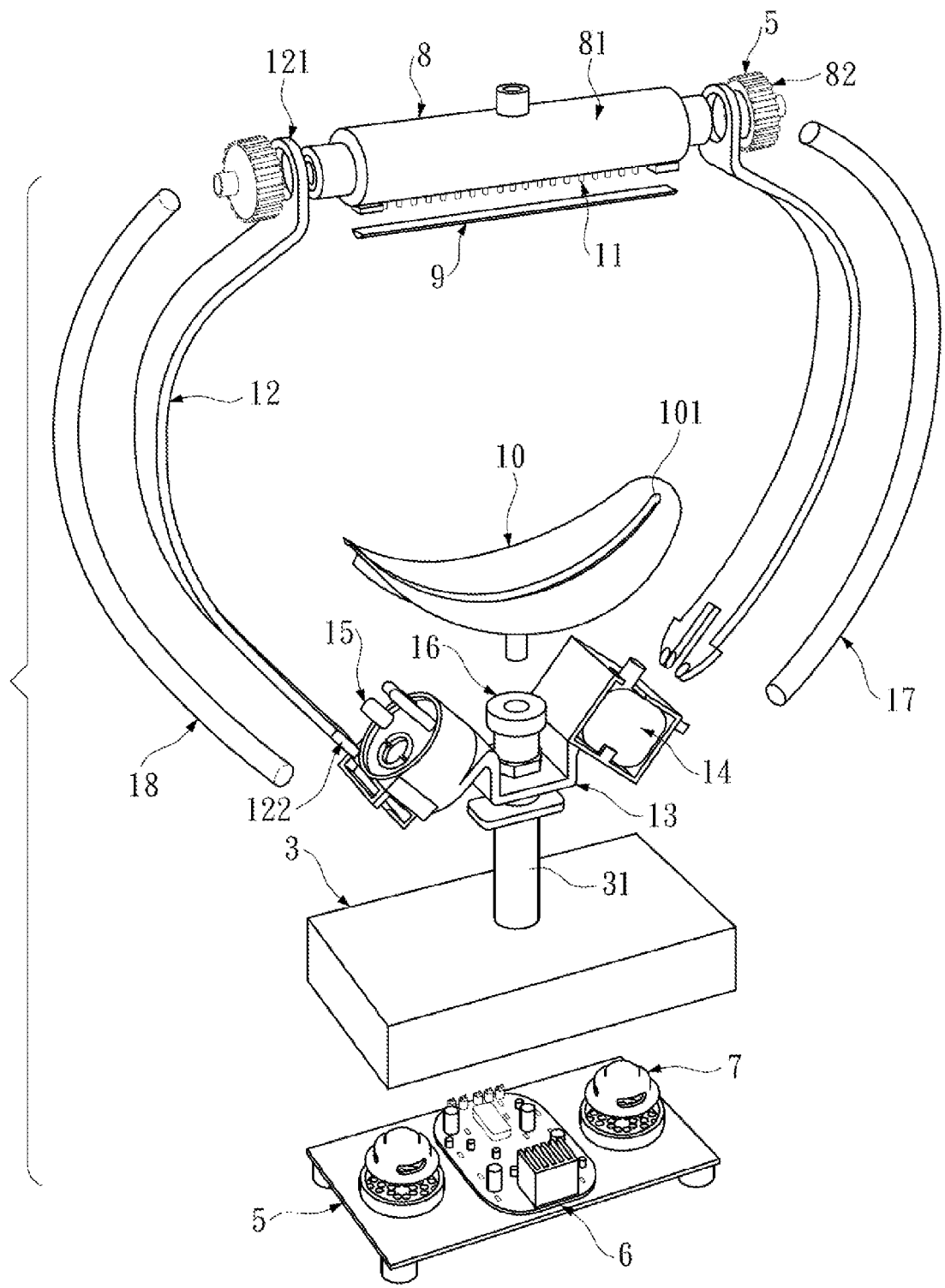
FIG. 2 is an exploded view of the present invention.
Figure 3:
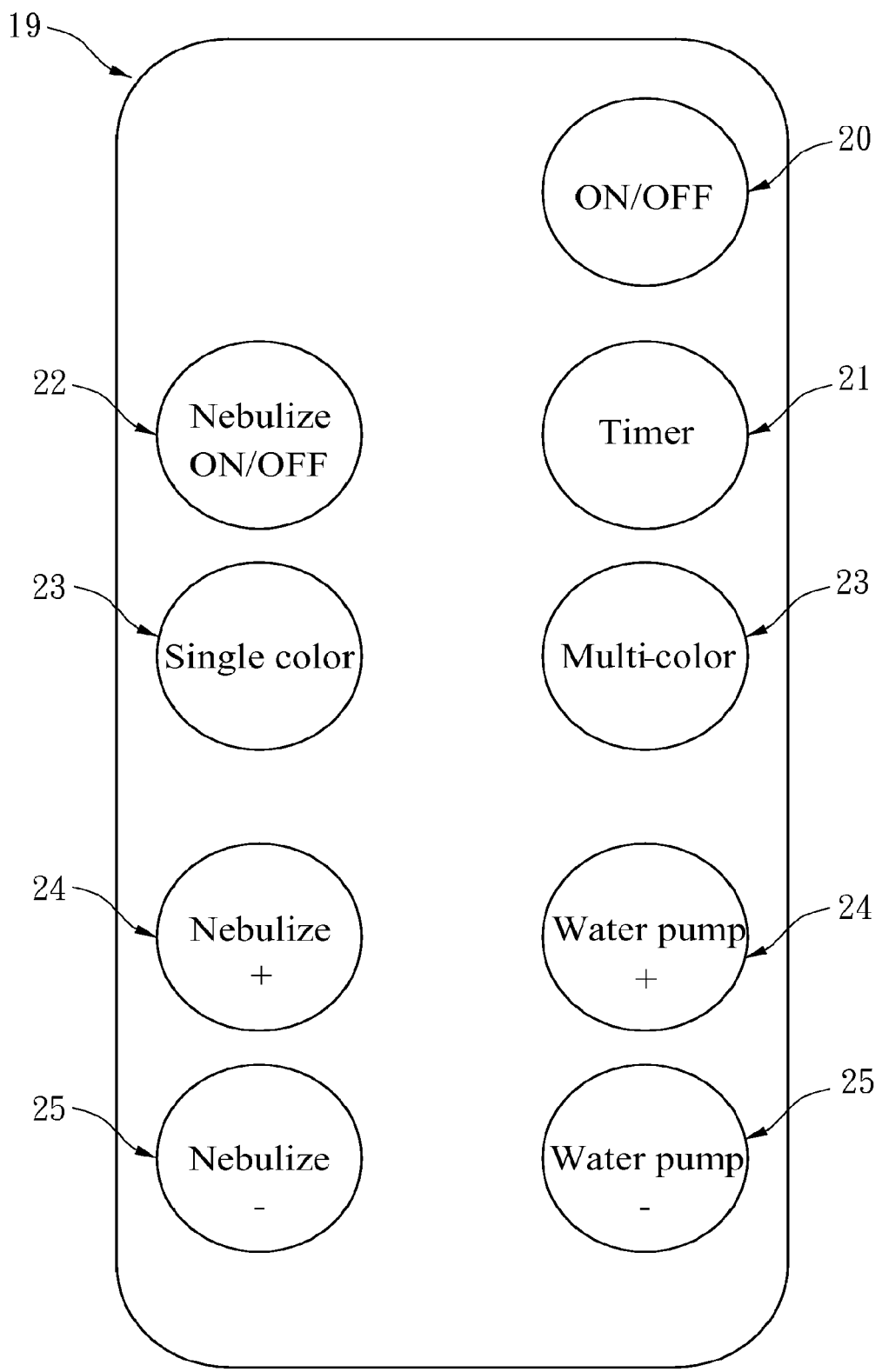
FIG. 3 is a front view of an infrared remote controller of the present invention.

With reference to FIGS. 1 to 3 for a structure of a wind-water ultrasonic humidifier in accordance with a preferred embodiment of the present invention, the structure is provided for the illustration of the present invention only, but not intended for limiting the scope of the invention.

In FIG. 1, the wind-water ultrasonic humidifier of the present invention comprises a ceramic housing 1, a water circulation system 2 installed in the housing 1, a bottom base 3 disposed at the bottom of the humidifier and a circuit retaining board 5 installed in the bottom base. The bottom of the bottom base 3 is a hollow structure for containing the circuit retaining board 5, and the middle of the top of the bottom base 3 has an opening interconnected with a hollow connecting portion, and the top of the hollow connecting portion has an externally threaded circular pipe 31 passed through a support plane with a circular hole at the bottom of the housing 1 and extended into the hollow housing 1, and then secured by a nut (not shown in the figure) for fixing the housing 1 with the bottom base 3. The ceramic housing is substantially in a circular shape or an elliptic shape, and the water circulation system 2 is disposed inside the housing 1. The circuit retaining board includes an integrated circuit board 6, a power adapter and a speaker 7.

With reference to FIG. 2 for an exploded view of a preferred embodiment of the present invention, the water circulation system 2 includes an electric base 13 installed at a position where the housing 1 and the bottom base 3 are connected, a hollow circular threaded pipe 31 passed through the bottom base 3 into the housing 1, and passed through the circular hole at the bottom of the electric base 13 and secured by the nut, so that the electric base can be fixed between the housing 1 and the bottom base 3. A rubber cork 16 is plugged precisely into the top of the circular threaded pipe 31 and having a concave hole, and a baffle 10 having a circular support pillar at the bottom of the baffle 10 is inserted into the concave hole of the rubber cork 16 for fixing the baffle 10 precisely above the rubber cork 16. The middle of the baffle 10 has a slender penetrating slot 101, such that when water drips, waterdrops fall onto a water level therebelow through the slender penetrating slot 101, and the baffle 10 is provided for preventing the dripping and sputtering of water.

The electric base 13 includes a circular cup-shaped containing space and a square containing space for installing the nebulizer 15 and the water pump 14 (as indicated by both sides of the circular hole in the figure) respectively.

Both sides of the electric base 13 are connected substantially into an arc shape by two arc bridging support stands 12, wherein the support stands 12 provide the effects of supporting and protecting the internal structure, and a lower end of the arc bridging support stand 12 has a protruded latching structure, and both sides of the electric base 13 are designed with a latch containing space for receiving the support stand latch.

An upper end of the bridging support stand 12 has a circular ring structure, and a water dripping device 8 is installed on an internal side of the bridging support stand 12. The water dripping device 8 is divided into three portions, whose middle portion is a circular level pipe 81, and portions on both sides are circular covers 82 with internal threads and having circular pipes protruded from the middle of external sides of the water dripping device 8 respectively, and both ends of the circular level pipe 81 at the middle portion of the water dripping device 8 are circular hollow platforms with external threads, and the circular ring structure 121 at the upper end of the bridging support stand 12 is passed through the circular hollow platform and coupled securely by the circular threaded covers 82 on both sides of the water dripping device 8. Two sections of water pipes 17, 18 are installed on both sides of the water dripping device 8 respectively, and top ends of the two water pipes 17, 18 are connected to the circular threaded covers 82 protruded from the center of external sides of a circular pipe 81 respectively, and the bottom of the inlet pipe 17 is connected to an exit of the water pump 14, and the bottom of the outlet pipe 18 is disposed above the level of water filled into the housing 1, and the two sections of water pipes are fixed onto external sides of the bridging support stand 12 by fixing devices.

The lower end of the circular level pipe 81 at the middle of the water dripping device 8 has a row of hollow protrusions 11 disposed vertically downward and having a diameter of 2 mm and a height of 8 mm, such that water flows from the water pump 14 into the water dripping device 8 through the inlet pipe 17, and a portion of water drops from the row of hollow protrusions 11 to a water level therebelow to achieve a raindrop effect, and another portion of water flows from the outlet pipe 18 connected to another end of the water dripping device 8 to a water level therebelow to achieve the water circulation function, and two square protrusions are disposed on a side of the row of hollow protrusions 11 at the lower end of the water dripping device 8 and have two circular holes fixed to a light emitting diode (LED) 9 for providing a colorful change of lighting.

The circuit and circuit control of the present invention are concentrated and installed on the circuit retaining board 5 at the bottom of the bottom base 3, and both ends of the circuit retaining board 5 have a circular through hole each, and a bolt is passed through the circular through hole to fix the bottom base, and the circuit retaining board 5 includes an integrated circuit board 6 and a speaker 7 installed thereon, cables of the light emitting diode (LED), water pump, nebulizer, and speaker connected to the circuit retaining board 5, as well as a power input slot, an audio input slot, an infrared sensor head and an LED timer indicating lamp. All functions of the present invention can be controlled by an external infrared remote controller 19.

With reference to FIG. 3 for a front view of a portion of an infrared remote controller 19 in accordance with the present invention, the infrared remote controller includes eight press buttons installed thereon. These press buttons are described below. A power ON/OFF press button 20 is provided for turning on or off the humidifier of the present invention and disconnecting an external audio playback. A timer press button 21 is provided for setting a timer of the humidifier of the present invention, such that when the set time is up, an LED timer indicating lamp is lit. For example, the humidifier can be set to be turned off automatically after being operated for two hours. A nebulization control press button 22 is provided for turning on or off a nebulizer independently, such that when the nebulizer is turned off, the water pump, the light emitting diode, and the audio playback are still operated normally to provide the desired raindrop, lighting and music effect. An LED light control press button 23 is provided for controlling the light emitting diode installed at the top of the humidifier of the present invention to selectively provide a colorful change of lighting or a single-color lighting. Two nebulization adjusting press buttons 24 are provided for controlling the level of nebulization of the nebulizer, and two water pump adjusting press buttons 25 are provided for adjusting the water pumping rate of the water pump and the speed of dropping waterdrops from the water dripping device, so as to provide various different raindrop effects.

In FIG. 1, a containing space is formed in the housing 1 of the wind-water ultrasonic humidifier of the present invention and provided for storing water and containing the water circulation system 2. A circular penetrating window 4 is designed at the center of the housing 1 and provided for filling water into the housing 1 and spraying mists from the window 4.

When the wind-water ultrasonic humidifier of the invention is operated, a 24VDC power is supplied from the power input slot, and water is filled from the penetrating window into the housing up to a marked level, and then the infrared remote controller is powered on, so that the humidifier of the invention starts operating, and the ultrasonic nebulizer produces natural dispersive water mists, and the water mists contain a large quantity of air anions and moisture to improve the air humidity and provide fresh air. The water pump pumps the water stored in the housing into the water dripping device through the inlet pipe, and a portion of water flows backs into the housing through an outlet pipe connected to the exit at another end of the water dripping device, and another portion of water drops from a row of hollow protrusions at the bottom of the water dripping device onto a water level therebelow to achieve a raindrop effect and provide a colorful change of lighting by the light emitting diode tubes connected to the bottom of the water dripping device, and the light can be adjusted by the LED lamp control press button of an infrared remote controller, such that a fancy colorful light changing effect can be produced selectively by the light emitting diode press button, and frames of the emitting color lights emitted from the light emitting diode can be held to produce a certain color. The lighting effect can be changed without limits and the frames of a certain lighting effect can be held selectively according to the user's personal preference. The audio input device is plugged and connected into the audio input slot of the bottom base, and pleasant high-fidelity music produced by an audio source is played by an amplification circuit and a stereo speaker on the integrated circuit board of the present invention. The nebulization adjusting press button on the infrared remote controller is provided for adjusting the quantity of mist produced by the nebulizer to fit different humidification requirements. The water pump adjusting press button is installed on the infrared remote controller for adjusting the quantity of sprayed water for various different raindrop effects according to user's personal preference. If the water level is below the required operating water level of the nebulizer, the nebulizer will detect the low water level and disconnect the power source, such that the water pump and the audio playback will be stopped automatically to prevent the nebulizer from working at a condition without water, and save unnecessary waste of power.

When the humidifier of the present invention is operated, the raindrop effect and the natural dispersive mist can be observed through the penetrating window of the housing, and the lights projected onto the waterdrops and mists of the water dripping device by the light emitting diode (LED) lamp are refracted to make the water drops crystal-clear and bright, so as to give a colorful misty atmosphere. With the sound of waterdrops and the music played by an audio source, a natural unique wind-water mind of state can be achieved, so that the humidifier further gives fantastic decorative and fun effects, in addition to the functions of the humidifier.

While the invention has been described by means of specific embodiments, numerous modifications and variations could be made thereto by those skilled in the art without departing from the scope and spirit of the invention set forth in the claims.

What is claimed is:

1. A wind-water ultrasonic humidifier, comprising:
    a housing;
    a hollow connecting portion, whose top is coupled to the bottom of said housing, for supplying electric power to said housing;
    a water circulation system, installed in said housing, and including an electric base disposed at the top of said connecting portion, a rubber cork plugged precisely into the top of said electric base and having a concave hole disposed at the top of said rubber cork, a baffle inserted into said concave hole of said rubber cork and having a cylindrical support pillar at the bottom of said baffle, and fixed precisely above said rubber cork, a slender penetrating slot formed at the middle of said baffle, a nebulizer and a water pump installed at both ends of said circular threaded pipe respectively, and both sides of said electric base being coupled into a substantially arc shape by two arc bridging support stands, and said support stand having a latching structure protruded from a lower end of said support stand, and both sides of said electric base having a latching space for receiving and latching said support stand, and said bridging support stand including a water dripping device installed at an upper end of said bridging support stand; and
    a power control box, installed at the bottom of said hollow connecting portion.

2. The wind-water ultrasonic humidifier of claim 1, wherein said water dripping device further includes a circular level pipe and a circular threaded cover having a protruded circular pipe installed on one external side of both sides of said circular threaded cover, and both ends of said circular level pipe have a circular hollow platform with an external thread, and a circular ring structure at the upper end of said bridging support stand is passed through said circular hollow platform and secured tightly with said circular threaded cover on both sides of said water dripping device, and an inlet pipe and an outlet pipe are disposed on both sides of said water dripping device respectively, and whose upper ends are coupled to said circular level pipe protruded from the center of an external side of said circular threaded cover, and a lower end of said inlet pipe is coupled to an exit of said water pump, and a lower end of said outlet pipe is disposed above a water level of water filled into said housing, and two sections of water pipes are fixed to external sides of said bridging support stand by fixing devices.

3. The wind-water ultrasonic humidifier of claim 2, wherein said water dripping device includes a row of hollow protrusions, each having a diameter of 2 mm and a height of 8 mm, arranged vertically downward, and disposed at a lower end of said circular level pipe, such that water flows from said water pump and is pumped to the inside through said inlet pipe, and a portion of water flows from said row of hollow protrusions and drips into a water level therebelow, and another portion of water flows from said outlet pipe connected to another end to the water level therebelow, and two square protrusions having two circular holes and disposed on a side of a row of hollow protrusions at the lower end of said water dripping device, and used together with screws for fixing a plurality of light emitting diodes (LEDs).

4. The wind-water ultrasonic humidifier of claim 3, wherein said power control box contains an integrated circuit board, a power adapter and a speaker.

5. The wind-water ultrasonic humidifier of claim 4, wherein said housing is made of a ceramic material.

* * * * *